US008669096B2

(12) United States Patent
Zhang et al.

(10) Patent No.: US 8,669,096 B2
(45) Date of Patent: Mar. 11, 2014

(54) SYSTEM AND METHOD FOR ISOLATION OF SAMPLES

(75) Inventors: Ye Zhang, League City, TX (US); Honglu Wu, Friendswood, TX (US)

(73) Assignee: The United States of America as represented by the Administrator of the National Aeronautics and Space Administration, Washington, DC (US)

( * ) Notice: Subject to any disclaimer, the term of this patent is extended or adjusted under 35 U.S.C. 154(b) by 0 days.

(21) Appl. No.: 13/461,487

(22) Filed: May 1, 2012

(65) Prior Publication Data

US 2013/0295652 A1 Nov. 7, 2013

(51) Int. Cl.
*C12N 1/08* (2006.01)
*B01D 21/00* (2006.01)

(52) U.S. Cl.
USPC ......... 435/270; 435/6.1; 435/287.1; 422/500; 422/527; 422/534; 422/537; 422/539

(58) Field of Classification Search
None
See application file for complete search history.

(56) References Cited

U.S. PATENT DOCUMENTS

| | | | | |
|---|---|---|---|---|
| 5,273,905 | A * | 12/1993 | Muller et al. | 435/286.5 |
| 6,110,730 | A | 8/2000 | Sams et al. | |
| 7,781,159 | B2 | 8/2010 | Gazenko | |
| 2002/0045246 | A1 * | 4/2002 | McMillan et al. | 435/306.1 |
| 2008/0153078 | A1 * | 6/2008 | Braman et al. | 435/2 |
| 2009/0011417 | A1 | 1/2009 | Maltezos et al. | |
| 2009/0280470 | A1 | 11/2009 | Fare et al. | |
| 2010/0159582 | A1 | 6/2010 | Ismail et al. | |
| 2010/0248350 | A1 | 9/2010 | Gazenko | |

* cited by examiner

*Primary Examiner* — Betty Forman
(74) *Attorney, Agent, or Firm* — Kurt G. Hammerle

(57) ABSTRACT

Systems and methods for isolating samples are provided. The system comprises a first membrane and a second membrane disposed within an enclosure. First and second reservoirs can also be disposed within the enclosure and adapted to contain one or more reagents therein. A first valve can be disposed within the enclosure and in fluid communication with the first reservoir, the second reservoir, or both. The first valve can also be in fluid communication with the first or second membranes or both. The first valve can be adapted to selectively regulate the flow of the reagents from the first reservoir, through at least one of the first and second membranes, and into the second reservoir.

16 Claims, 11 Drawing Sheets

SYSTEM AND METHOD FOR ISOLATION OF SAMPLES

ORIGIN OF THE INVENTION

The invention described herein was made in the performance of work under a NASA contract and is subject to the provisions of Section 305 of the National Aeronautics and Space Act of 1958, Public Law 85-568 (72 Stat. 435; 42 U.S.C. 2457).

BACKGROUND

Field

Embodiments described herein generally relate to apparatus, systems, and methods for isolation of samples, such as samples containing nucleic acid, cells, proteins, or chemical materials.

SUMMARY

This summary is provided to introduce a selection of concepts that are further described below in the detailed description. This summary is not intended to identify key or essential features of the claimed subject matter, nor is it intended to be used as an aid in limiting the scope of the claimed subject matter.

Systems and methods for isolating samples are provided. The system can include first and second membranes disposed within an enclosure. First and second reservoirs can also be disposed within the enclosure and adapted to contain one or more reagents therein. A first valve can be disposed within the enclosure and in fluid communication with the first reservoir, the second reservoir, or both. The first valve can also be in fluid communication with the first membrane, the second membrane, or both. The first valve can be adapted to selectively regulate the flow of the reagents from the first reservoir, through at least one of the first and second membranes, and into the second reservoir. A second valve can be disposed within the enclosure and in fluid communication with the first reservoir, the second reservoir, or both. The second valve can also be in fluid communication with the first membrane, the second membrane, or both. The second valve can be adapted to selectively regulate the flow of the reagents from the first reservoir, through at least one of the first and second membranes, and into the second reservoir.

The method includes flowing a first reagent from a first reservoir through a first membrane and a first valve and into a second reservoir containing a second reagent to form a first mixture including the first and second reagents. The first mixture then flows through the first valve, a second valve, and a second membrane and into a third reservoir.

DETAILED DESCRIPTION

Figure 1:
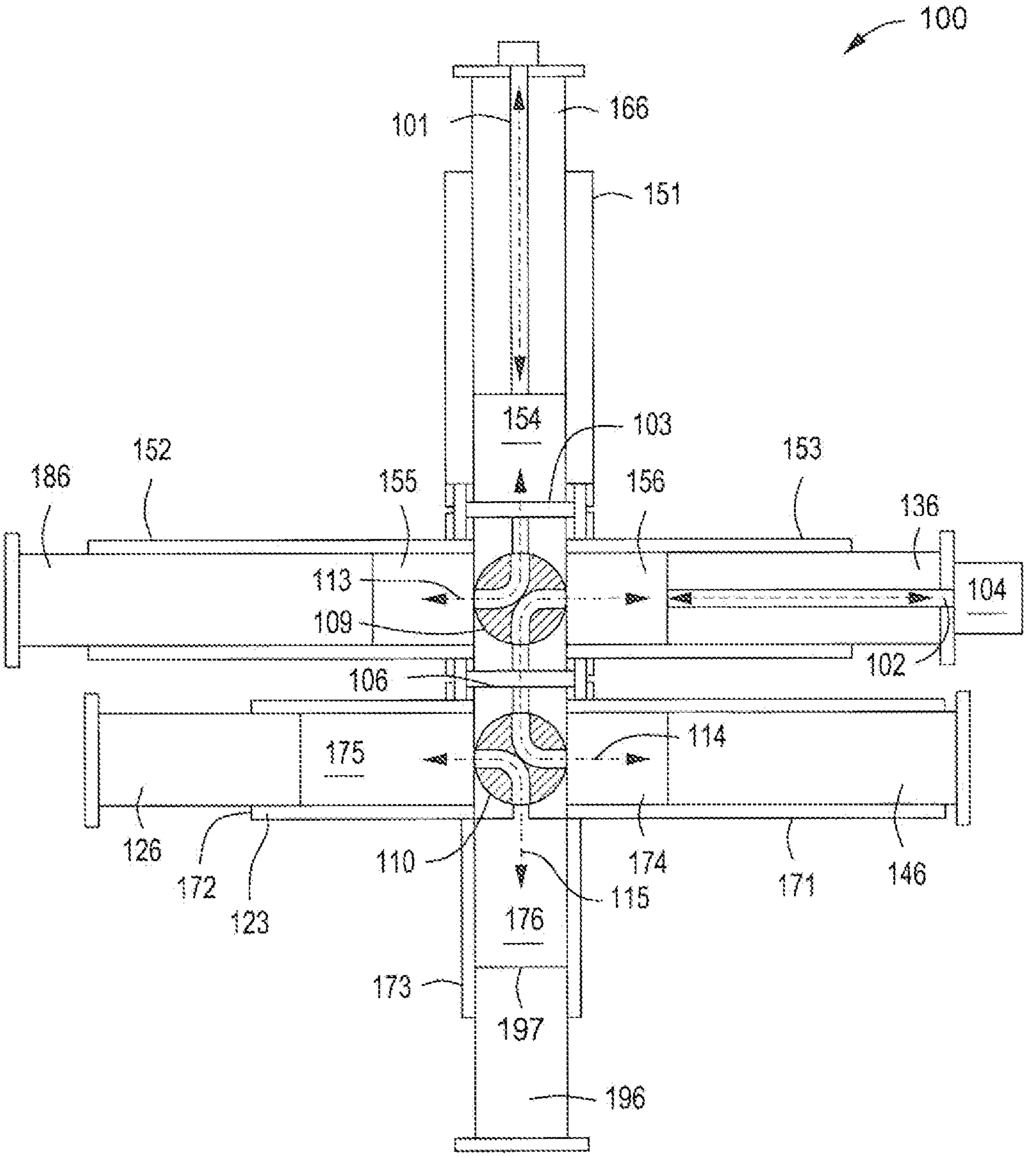
FIG. 1 depicts a cross-sectional view of an illustrative sample isolation system, according to one or more embodiments described.
Figure 2:
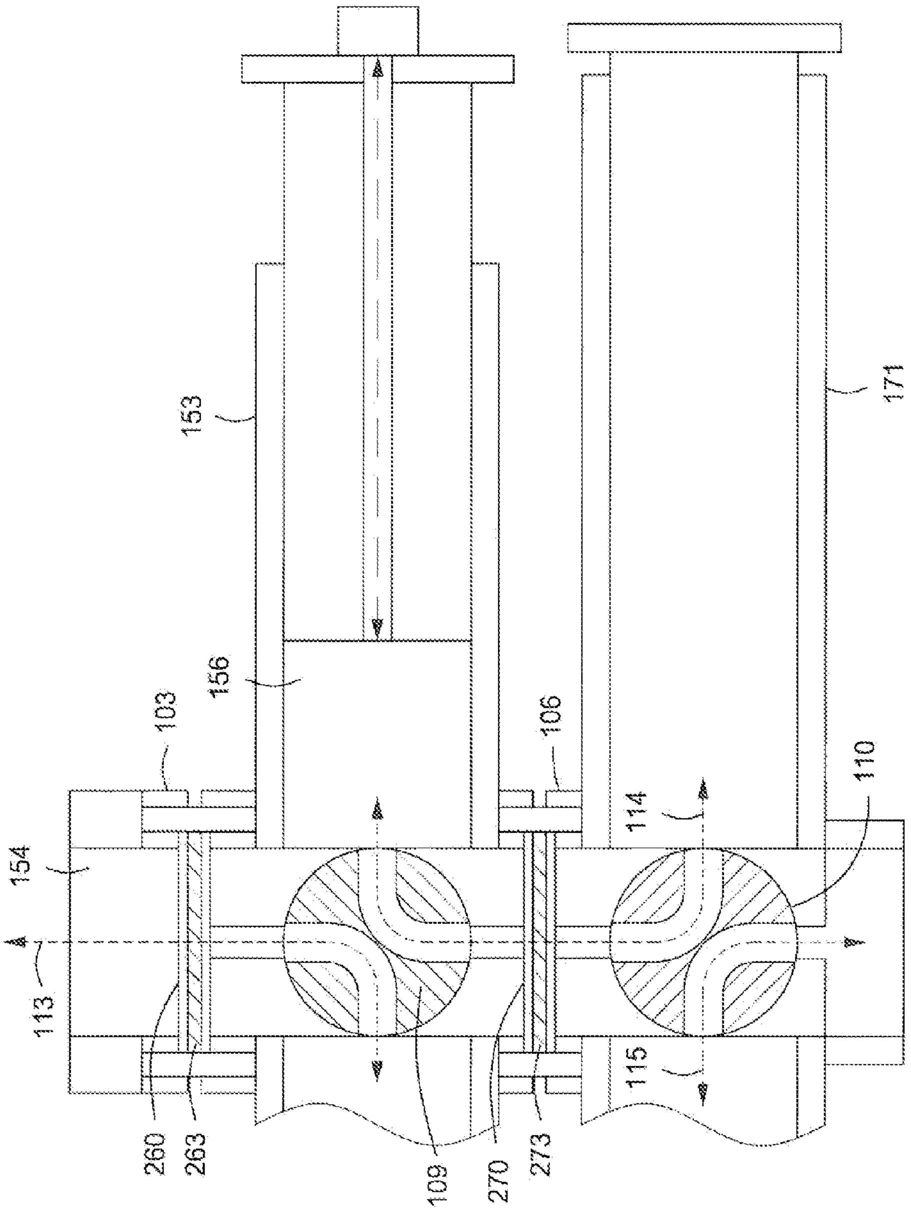
FIG. 2 depicts a partial close-up view of the sample isolation system depicted in FIG. 1, according to one or more embodiments described.

FIG. 1 depicts a cross-sectional view of an illustrative sample isolation system or enclosure 100, and FIG. 2 depicts a partial close-up view of the sample isolation system 100 depicted in FIG. 1. The isolation system 100 is a pipette-free, closed or self-contained system. As a closed or self-contained system, fluid disposed within the system 100 does not escape or leak out, as would occur with traditional open-ended pipettes. Given that the system is self-contained, it may be used in environments in which it is desirable to minimize the escape of samples or the exposure to contaminants. One example of such environment is a microgravity environment, such as the International Space Station. Another example might be a terrestrial environment such as a clean room or a laboratory for biosafety.

Two or more membrane support assemblies 103, 106 can be contained or encapsulated within the isolation system 100. Each support assembly 103, 106 can include one or more support members 260, 270 for holding or supporting a membrane 263, 273. In at least one embodiment, the support members 260, 270 can be perforated and disposed adjacent opposing surfaces of the membranes 263, 273 such that the membranes 263, 273 are disposed within the support members 260, 270. The term "membrane," as used herein, refers to any material or layers of material that act as a selective barrier, allowing selected fluids and/or particles to pass therethrough, or in other embodiments allowing items of interest, such as proteins, molecules, cells, or particles, to be instead retained therein. As such, fluid and/or particles can flow or pass through the support members 260, 270 and the membranes 263, 273 while other items of interest bind to the membranes 263, 273.

Suitable membranes can include one or more micropores. The micropores can have an average pore diameter ranging from a low of about 0.2 μm, about 0.4 μm, or about 0.6 μm to a high of about 1 μm, about 2 μm, about 3 μm, about 4 μm, or about 5 μm, such as a membrane suitable for RNA/DNA isolation. However, for other applications, the micropores can have an average pore diameter ranging from a low of about 0.0001 μm, about 0.001 μm, or about 0.01 μm to a high of about 0.05 μm, about 0.1 μm, or about 0.2 μm (e.g., for protein isolation or separation), or from a low of about 10 μm, about 20 μm, or about 30 μm to a high of about 50 μm, about 75 μm, or about 100 μm (e.g., for filtering single cell suspension). The membranes can also be used for binding, isolating, and separating specific molecules and particles, isolating specific types of cells, and reagent sterilization.

In one embodiment, a sample of interest, such as blood, saliva, urine, buffy coat, bacterial cultures, and the like containing nucleic acid, can be placed on the "first" or "sample" membrane 263. In at least one embodiment, the sample can be placed directly on the first membrane 263, and the first membrane 263 can then be placed within a support member 260 of the support assembly 103. The support assembly 103 can then be disposed within the isolation system 100.

The first membrane 263 and/or the "second" or "binding" membrane 273 can be, but are not limited to, a proteinase membrane, a homogenizing membrane, a filtering membrane, a binding membrane, or any combination thereof. For example, the first membrane 263 can be a proteinase membrane containing the sample, and the second membrane 273 can be a binding membrane that acts as a platform or surface to bind precipitated nucleic acids released from the first membrane 263, while not absorbing potentially contaminating proteins or other biologic agents. Suitable commercially available membranes can include, but are not limited to, membranes found in standard kits for the purification of DNA or RNA sold commercially by the manufacturer Qiagen (e.g., DNeasy® Blood and Tissue Kit, RNeasy® Mini Kit, RNeasy® Protect Mini Kit, and RNeasy® Plant Mini Kit).

Suitable membranes 263, 273 can also include a solid surface functionalized with immobilized active enzymes and high density enzyme surfaces. More specifically, membranes for use with the present sample isolation system 100 can include a solid surface functionalized with immobilized proteinase, such as trypsin, chymotrypsin, endoproteinase GluC, papain, endoproteinase pepsin, proteinase K, and the like. Suitable solid surfaces can also include glass fiber, glass fiber treated with oleophobic coatings, silica particles or beads, silica particles or beads coated with oleophobic coatings, nylon, and other oleophobic materials, and the like. For example, suitable membranes can include the DigesTip™ produced by the manufacturer ProteoGen Bio in Siena, Italy. In at least one embodiment, the surface can be coated with complementary oligo nucleictides, antibodies, covalently or non-covalently binding to target molecules, and/or any particles and membranes used for separating molecules based on size and isoelectric point.

One or more valves (two are shown in FIGS. 1 and 2 as parts 109, 110) and one or more injectors (six are shown in FIGS. 1 and 2 as parts 151, 152, 153, 171, 172, 173) can also be located within the sample isolation system 100. In at least one embodiment, the membrane support assemblies 103, 106, the valves 109, 110, and the injectors 151, 152, 153, 171, 172, 173 can be coupled together to form the enclosed isolation system 100. The components may be coupled in any manner known in the art to form an air-tight enclosure for use in closed or self-contained environments. For example, the components can be threaded together. In at least one embodiment, tubing (not shown) having a diameter similar to the diameter of the flow path through the valves 109, 110 (e.g., 15-gauge tubing) can be coupled to and disposed between the injectors 151, 152, 153, 171, 172, 173 and the valves 109, 110 to provide more flexibility to the sample isolation system 100.

The first membrane support assembly 103 can be threadably engaged or otherwise operatively connected in a manner so as to prevent leaks of fluid or particles between the first injector 151 and the first valve 109. The second membrane support assembly 106 can be threadably engaged or otherwise operatively connected in a manner to prevent leaks of fluid or particles between the first valve 109 and the second valve 110. The second and third injectors 152, 153, respectively can be threadably engaged or otherwise operatively connected in a sealed manner with the first valve 109. The fourth, fifth, and sixth injectors 171, 172, 173, respectively, can be threadably engaged or otherwise operatively connected in a sealed manner with the second valve 110. As may be appreciated by the skilled artisan having the benefit of the description contained herein, the components may be coupled together in any other suitable configuration, and any number of valves and/or injectors can be used.

In one embodiment, the valves 109, 110 each include a rotatable housing having at least one bore (two are shown in FIGS. 1 and 2 such that the valves are four-way valves) formed therethrough. As such, the valves 109, 110 can be actuated or rotated such that one or more flow paths 113, 114, 115 (as illustrated by two-way vectors) can provide fluid communication from a first reservoir disposed within one injector (151, 152, 153, 171, 172, 173) through at least one of the valves (109, 110) and into a second reservoir of another injector (151, 152, 153, 171, 172, 173). As shown in FIG. 1, the first and second valves 109, 110 are oriented such that the flow path 113 extends between the first injector 151 and the second injector 152 (through the first membrane 263), the flow path 114 extends between the third injector 153 and the fourth injector 171 (through the second membrane 273), and the flow path 115 extends between the fifth injector 172 and the sixth injector 173. However, as may be appreciated by the skilled artisan having benefit of this description, the first and second valves 109, 110 can be rotated to vary the flow paths 113, 114, 115, into other flow paths as will be described in more detail below.

The flow paths 113, 114, 115 can, at least in part, depend on the type of valves 109, 110 used and/or the configuration of the valves 109, 110 in relation to the other components of the sample isolation system 100. In one embodiment, suitable valves 109, 110 with a rotatable housing can be or include valves manufactured and commercially sold by the Hamilton Company of Reno, Nev. Further, the flow paths 113, 114, 115 can be unidirectional and/or bidirectional (as indicated by the two-way vectors). In one embodiment, a solution and/or reagent can be both drawn into and/or discharged from an injector 151, 152, 153, 171, 172, 173 or any other component of the sample isolation system 100, along the flow paths 113, 114, 115.

The valves 109, 110 can be one-way valves (e.g., check valve) and/or multi-way valves (e.g., two-way, three-way, or four-way valves). The valves 109, 110 can further include a control unit (not shown) that can selectively rotate the valves 109, 110 to provide the desired flowpaths of interest, such as the flowpaths 113, 114, 115. The control unit can include, but is not limited to, a manual handle connected to the valves 109, 110 and/or an electronic actuator. For example, a manual handle or switch coupled to the valves 109, 110 can be rotated by the user to select the desired setting of the valves 109, 110 and to selectively form the flow paths (such as 113, 114, 115) desired through the sample isolation system 100.

The injectors 151, 152, 153, 171, 172, 173 can further include one or more chambers or reservoirs (six are shown as corresponding parts 154, 155, 156, 174, 175, 176, respectively) for storing reagents or other fluids used for the sample isolation process. In at least one embodiment, a bore 101 can be formed through a piston 166 in the first injector 151 to provide a path of fluid communication through to the reservoir 154 of the first injector 151. In at least one embodiment, the sample of interest can be inserted into the system 100 via the bore 101. Further, the bore 101 and/or the reservoir 154 of the first injector 151 can be sonicated to mix or agitate the sample and/or reagent disposed therein.

A bore 102 can also be formed through a piston 136 of the third injector 153 to provide a path of fluid communication through to the reservoir 156 of the third injector 153. In at least one embodiment, a vacuum or other device 104 can be in fluid communication with the bore 102 and adapted to increase or decrease the pressure within the system 100. Further, the vacuum 104 can be adapted to dry the first and/or second membranes 263, 273.

The reagents used within the system 100 can be or include any fluid for molecular and/or cellular isolation techniques and can be used in any amount. Such reagents can include one or more lysing and denaturing substances and/or one or more buffer solutions. In at least one embodiment, a first reagent can be or include a phosphate buffer solution (PBS), a salt, a detergent, an alcohol, or a protease, and a second reagent can include a lysis buffer such as a solution containing guanidinium chloride, which helps break open cells and their nuclei to extract deoxyribo nucleic acid (DNA) for analysis. One example of a lysis buffer sold commercially is the product named "Buffer AL" sold by the manufacturer Qiagen. In another embodiment, the detergent can be a quaternary amine cationic detergent such as cetyltrimethylammonium bromide (CTAB), Guanidine thiocyanate (GuSCN), and the like, and/or the protease can be trypsin, chymotrypsin, endoproteinase GluC, papain, endoproteinase pepsin, proteinase K, and the like. For example, the first reagent can include from a low of about 0.1 mL, about 0.2 mL, about 0.4 mL, about 0.6 mL, about 0.8 mL, or about 1.0 mL to a high of about 2.0 mL, about 3.0 mL, about 4.0 mL, about 5.0 mL, or more of PBS, an alcohol solution, a detergent solution, or a combination thereof. The second reagent can include from a low of about 0.1 mL, about 0.2 mL, about 0.4 mL, about 0.6 mL, about 0.8 mL, or about 1.0 mL to a high of about 2.0 mL, about 3.0 mL, about 4.0 mL, about 5.0 mL, or more of a lysis buffer.

In another embodiment, the first reagent can include a lysis buffer, and the second reagent can include an alcohol solution. The first reagent can include from a low of about 0.1 mL, about 0.2 mL, about 0.4 mL, about 0.6 mL, about 0.8 mL, or about 1.0 mL to a high of about 2.0 mL, about 3.0 mL, about 4.0 mL, about 5.0 mL, or more of the lysis buffer. The second reagent can include from a low of about 0.1 mL, about 0.2 mL, about 0.4 mL, about 0.6 mL, about 0.8 mL, or about 1.0 mL to a high of about 2.0 mL, about 3.0 mL, about 4.0 mL, about 5.0 mL, or more of the alcohol solution. The alcohol solution can contain from a low of about 50%, about 60%, or about 70% to a high of about 80%, about 90%, or about 95% ethanol.

Figure 3:
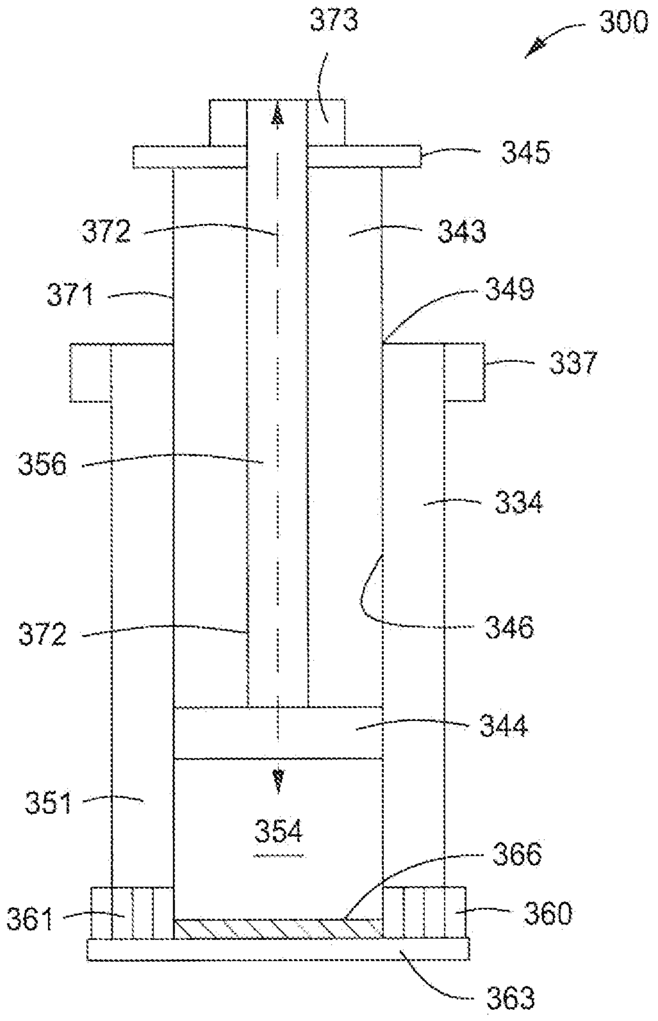
FIG. 3 depicts a cross-sectional view of an illustrative injector that can be integrated or coupled to one or more components of the sample isolation system, according to one or more embodiments described.
Figure 4A:
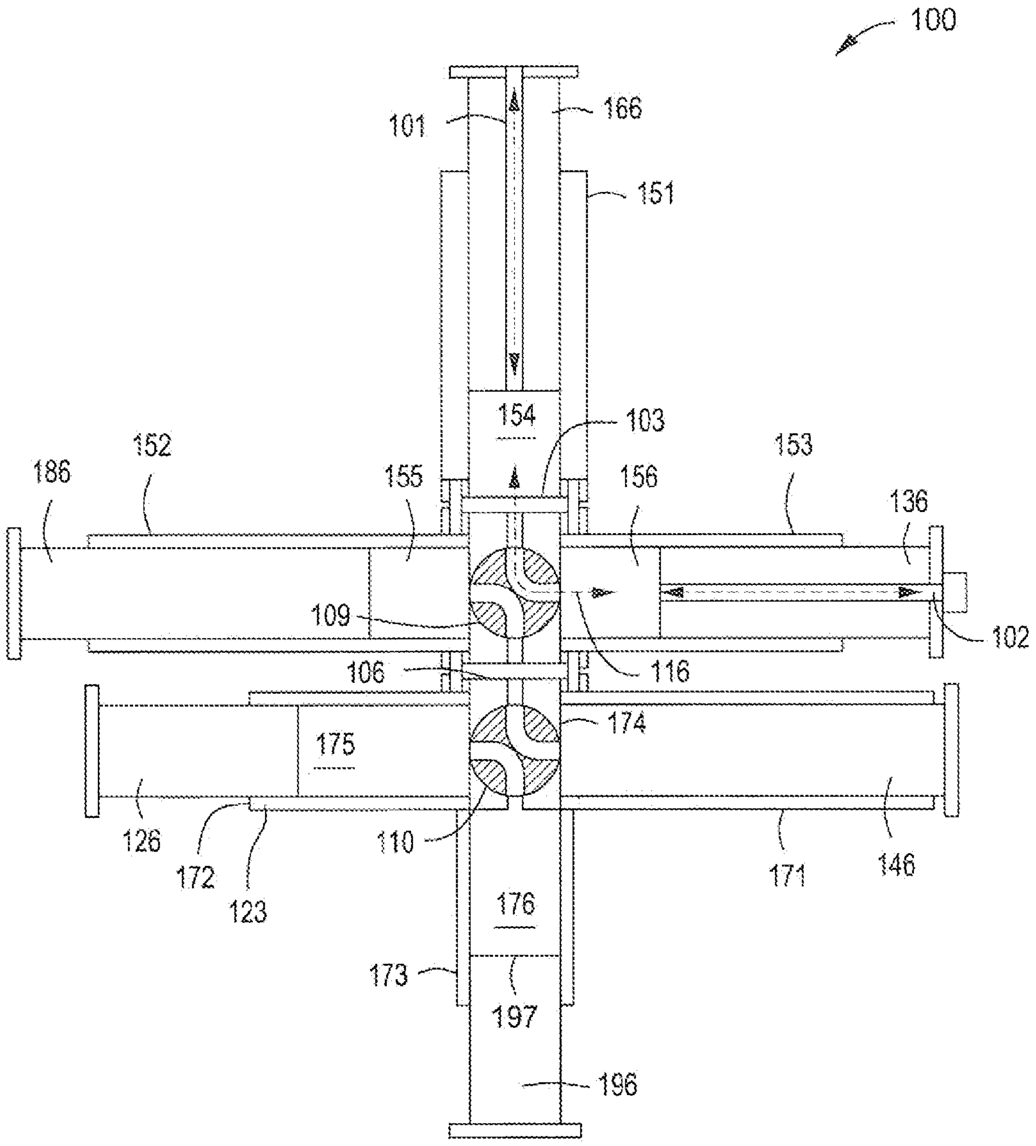
FIGS. 4A-E depict cross-sectional views of the sample isolation system during a DNA isolation process, according to one or more embodiments described.
Figure 4B:
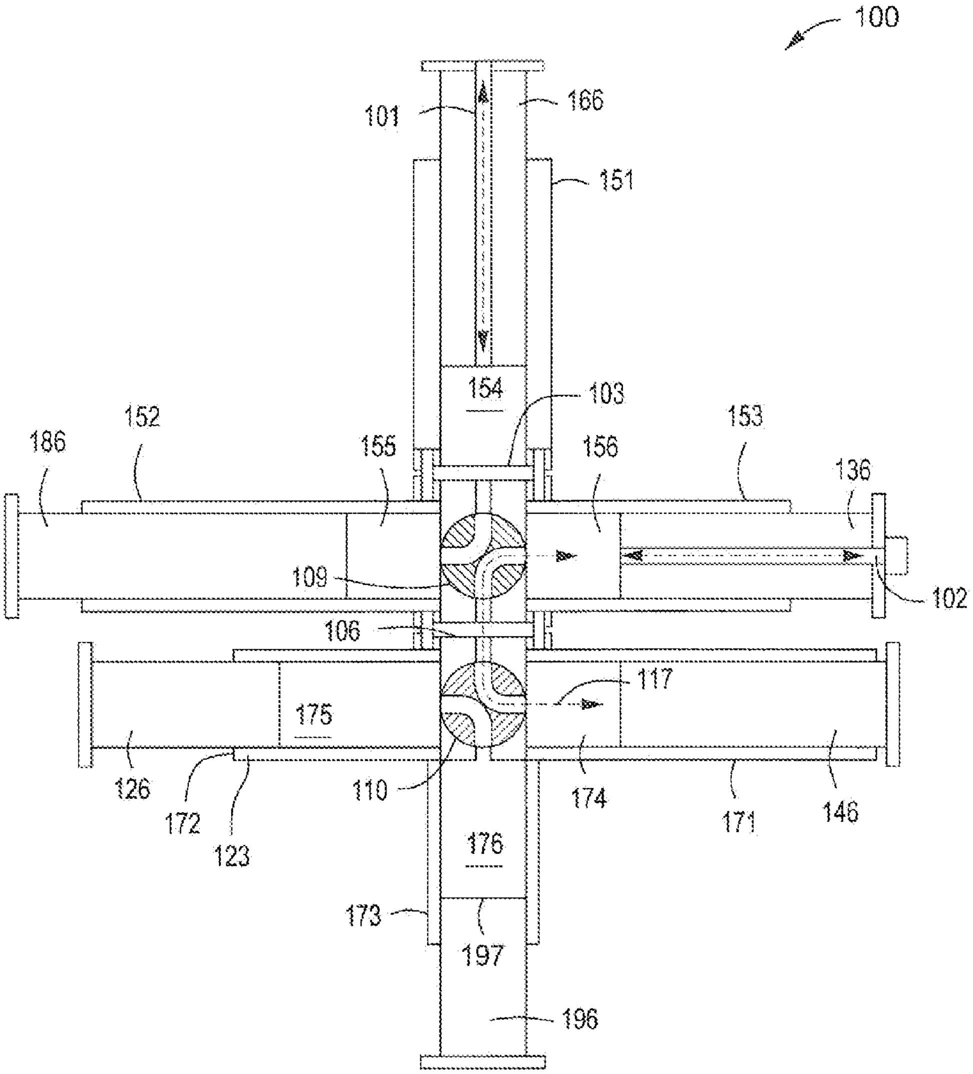
Figure 4C:
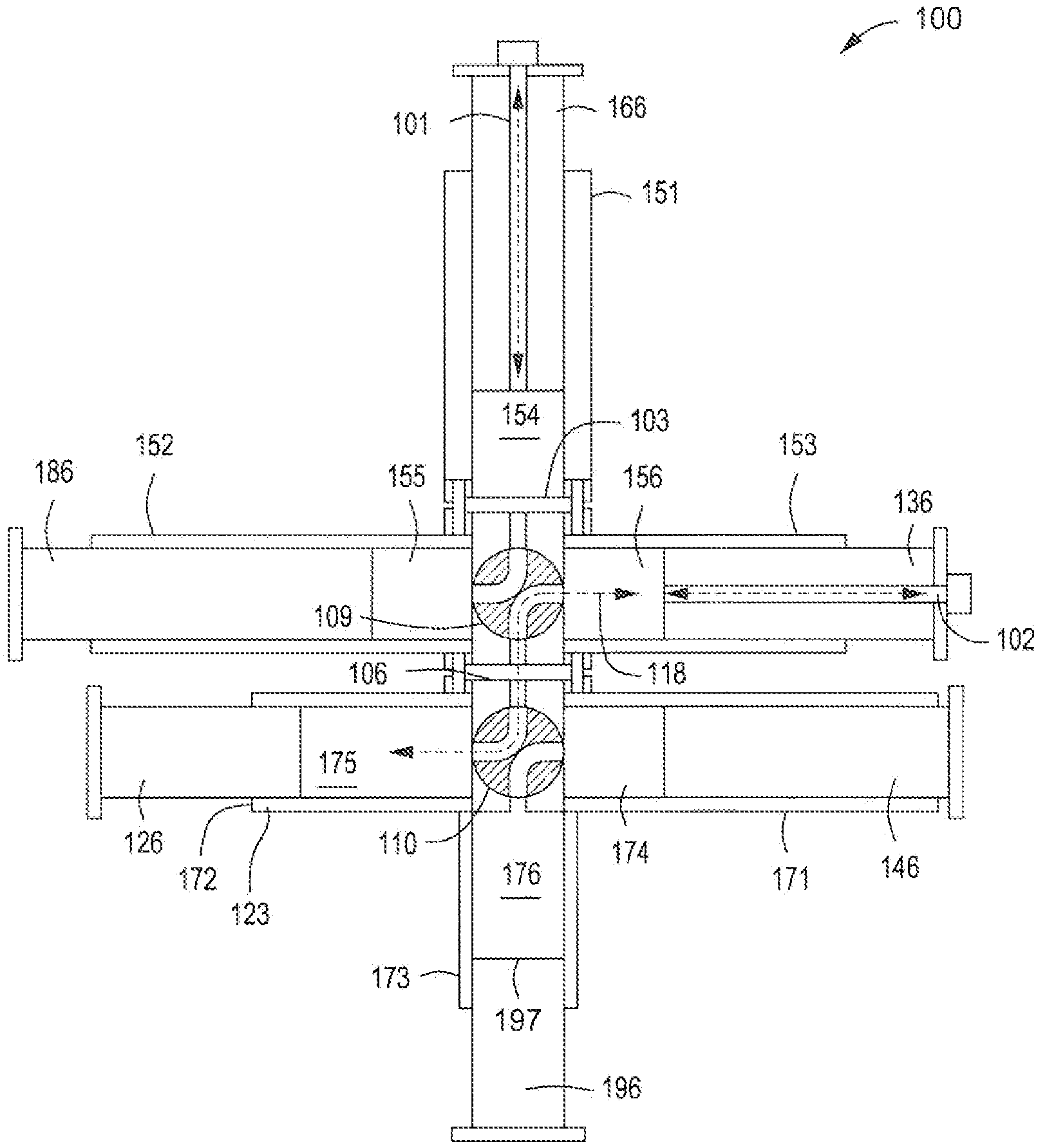
Figure 4D:
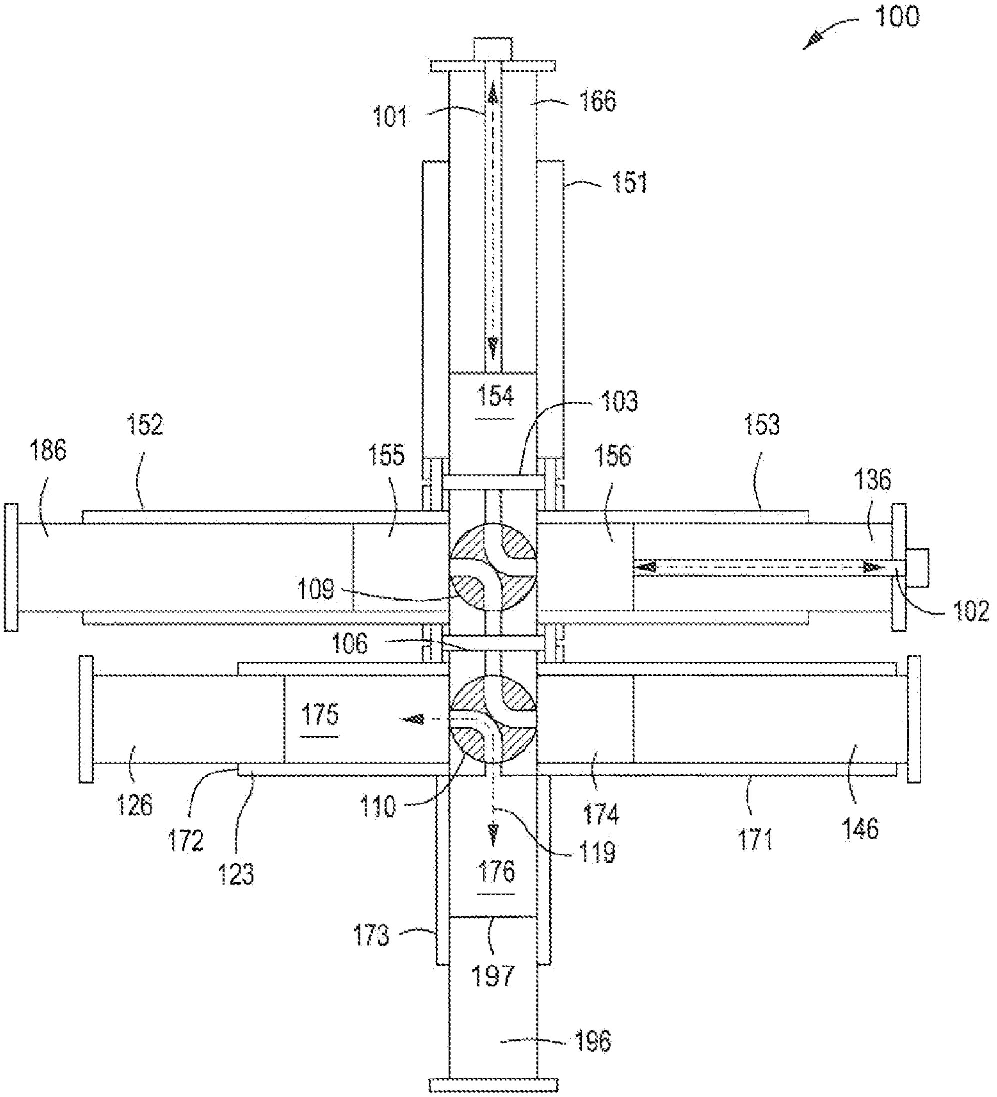
Figure 4E:
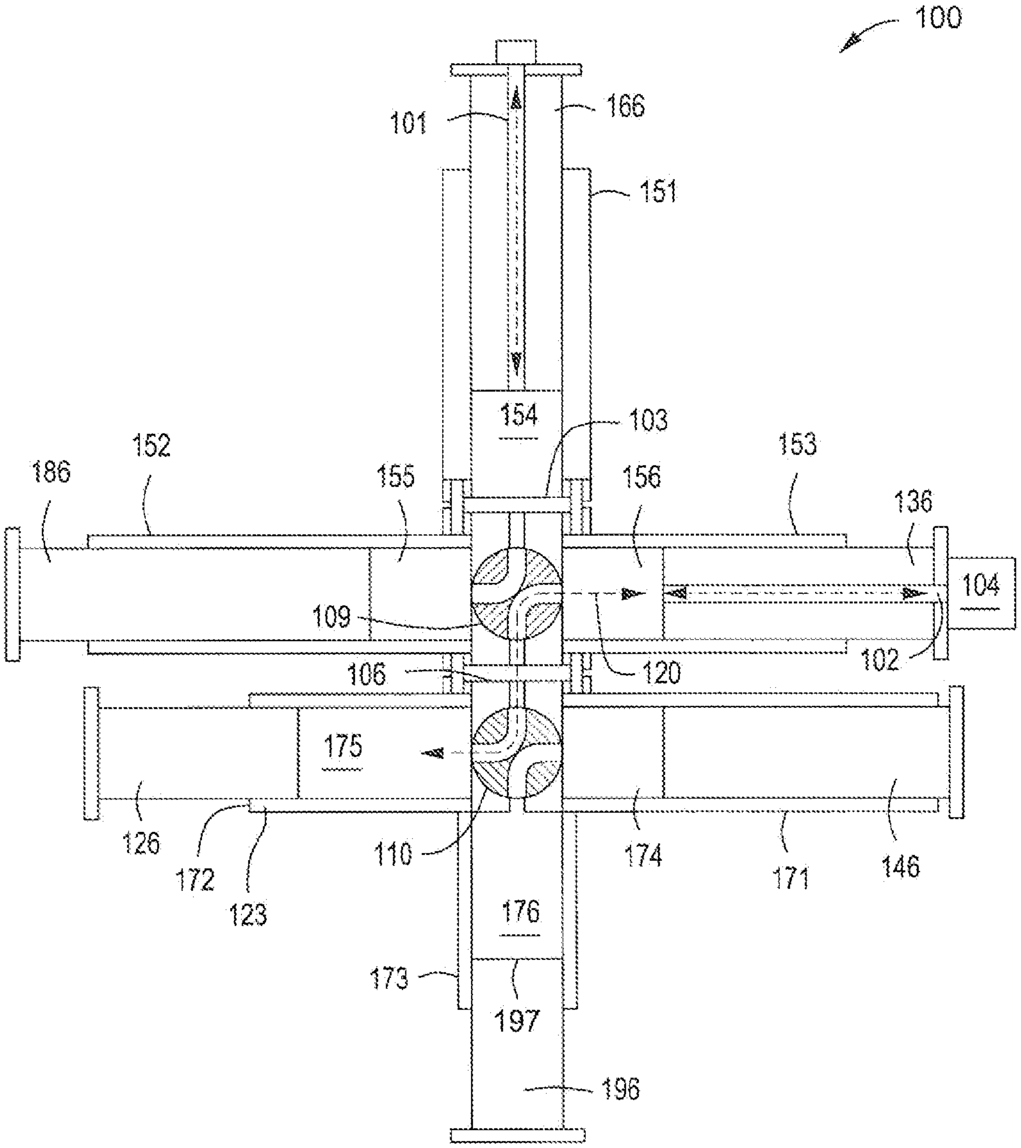

FIG. 3 depicts a cross-sectional view of an illustrative injector 300 that can be integrated or coupled to one or more components of the sample isolation system 100, according to one or more embodiments. The injector 300 can be designed for handling biological samples, and it can be assembled anywhere within the system 100. The injector 300 can be similar to the injectors 151, 152, 153, 171, 172, 173 shown and described above. For example, the injector 300 can include a body 334 having a first end 351 and a second end 349. The body 334 can include an inner surface 346 that defines a bore or passageway completely or at least partially therethrough. A piston 343 can be disposed within at least a portion of the bore. A reservoir 354 can be formed between the piston 343 and the first end 351 of the body 334.

The injector 300 can further include one or more caps (one is shown in FIG. 3 as 363), one or more membranes (one is shown as 366), one or more unitized finger grips (one is shown as 337), and one or more couplers (one is shown as 361). The cap 363 of the injector 300 can be coupled to one or more ends 349, 351 of the body 334 of the injector 300. FIG. 3 illustrates the cap 363 coupled to the open first end 351 of the body 334 through the coupler 360. The cap 363 can also be coupled to the body 334 through any appropriate means previously discussed including, but not limited to, one or more clamps, straps, latches, snap-fit mechanisms, pipe-fittings, pipe-threading, or other fasteners, or any combination thereof. Coupling of the cap 363 to the body 334 can substantially enclose or seal the one or more ends 349, 351 of the body 300. The cap 363 can also, at least in part, define the reservoir 354 of the injector 300.

The membrane 366 of the injector 300 can be disposed on or within the injector 300 and can form a seal with the inner wall 346 of the body 334. For example, the membrane 366 in FIG. 3 is disposed on the open first end 351 of the body 334, spanning the cross-section of the inner wall 346. The membrane 366 can be similar to the membranes 263, 273 described above, and thus, will not be described again in detail.

The piston 343 of the injector 300 can include a plunger 344 on one end and an integrated thumb tab 345 on the other end. As shown in FIG. 3, the plunger 344 can form a seal with the inner wall 346 of the body 334. The thumb tab 345 is capable of maneuvering the piston 343 in a sliding engagement back and forth along the inner wall 346 by applying a force upon the piston 343. The force upon the piston 343 can be applied in a first direction toward the first end 351 or in a second direction toward the second end 349. The force applied upon the piston 343 can be from one or more passive or active sources and can be a negative pressure or positive pressure. For example, the pressure applied upon the piston 343 can be from an automated actuator, an increase or decrease in the size of the reservoir 354 of the injector 300, an applied pressure on the thumb tab 345, an applied pressure from the plunger 344, or any combination thereof.

A bore 356 can extend through the piston 343 and be in fluid communication with the reservoir 354. The bore 356 can be sealed with a plug or sealing member 373, or by other devices, such as a quick-connect coupler, a pierceable self-resealable elastic stopper (e.g. rubber septum), or any combination thereof. The bore 356 can include a vacuum line connection, a sonicator, a homogenizer, or the like coupled to or in fluid communication therewith. The vacuum can be adapted to vary the pressure within the system 100 and/or dry the membrane 366.

In at least one embodiment, the bore 356 can be used to introduce the biological sample to the system 100. In another embodiment, the reservoir 354 can include a first reagent, the bore 356 can include a second reagent, and an additional membrane (not shown) can be positioned between the bore 356 and the reservoir 354 in the general vicinity of the plunger 344.

In at least one embodiment, the injector 300 (or any injector in the system 100) can include a heater, a micro-magnet, and/or an interface that can receive a spectrophotometer. The end of the plunger 344 can be the platform for array analysis, including, but not limited to, anchoring complementary cDNAs, antibodies, or other molecules, which specifically recognize target molecules.

FIGS. 4A-E depict cross-sectional views of the sample isolation system 100 during an exemplary isolation process, according to one or more embodiments. Referring now to FIGS. 1 and 4A-E, in operation, the sample, such as a blood sample containing nucleic acids, can be placed on the first membrane 263 of the membrane support assembly 103. The membrane support assembly 103 can then be disposed within the sample isolation system 100. The first valve 109 can be selectively rotated to provide a first flow path 113 (see FIG. 1) between the first injector 151 and the second injector 152 through the first valve 109 and the first membrane 263.

The first reservoir 154 can have the first reagent disposed therein, and the second reservoir 155 can have the second reagent disposed therein. The piston 166 of the first injector 151 can be moved to decrease the volume of the first reservoir 154, thereby forcing the first reagent through the first flow path 113 and into the second reservoir 155 of the second injector 152. Thus, the first reagent can flow through the first valve 109 and first membrane 263 before entering the second reservoir 155 of the second injector 152. When the first reagent contacts the first membrane 263, the cells can be disrupted and the nucleic acids can be released. Accordingly, the first reagent and the released nucleic acids can be combined with the second reagent in the second reservoir 155 to form a first mixture.

The piston 186 of the second injector 152 can subsequently be moved to decrease the volume of the second reservoir 155, thereby forcing the first mixture through the first flow path 113 and back into the first reservoir 154. This process can be subsequently repeated one or more times to ensure complete mixture of the first and second reagents and to ensure a complete interaction between the first mixture with the first membrane 263. Once mixing is complete, the first mixture can then be forced back into the reservoir 154 of the first injector 151.

The first valve 109 can be then be selectively rotated to provide a second flow path 116 (see FIG. 4A) between the first reservoir 154 and the third reservoir 156 through the first valve 109 and the first membrane 263. The reservoir 156 of the third injector 153 can include a third reagent. In at least one embodiment, the third reagent can include an ethanol solution. For example, the reservoir 156 of the third injector 153 can include from a low of about 0.1 mL, about 0.2 mL, about 0.4 mL, about 0.6 mL, about 0.8 mL, or about 1.0 mL to a high of about 2.0 mL, about 3.0 mL, about 4.0 mL, about 5.0 mL, or more of the solution. The solution can contain from a low of about 50%, about 60%, or about 70% to a high of about 80%, about 90%, or about 95% ethanol. The piston 166 of the first injector 151 can then be moved to decrease the volume of the first reservoir 154, thereby forcing the first mixture through the second flow path 116 and into the third reservoir 156 of the third injector 153. Thus, the first mixture can flow through the first valve 109 and first membrane 263 before entering the third reservoir 156 of the third injector 153, thereby combining the first mixture and the third reagent to form a second mixture. The piston 136 of the third injector 153 can then be moved to decrease the volume of the third reservoir 156, thereby forcing the second mixture through the second flow path 116 and back into the first reservoir 154 of the first injector 151. This process can be repeated one or more times. The second mixture can then be forced back into the third injector 153.

The first and second valves 109, 110 can be then be selectively rotated to provide a third flow path 117 (see FIG. 4B) between the third reservoir 156 and the fourth reservoir 174 through the first and second valves 109, 110 and the second membrane 273. The reservoir 174 of the fourth injector 171 can define an empty volume. The piston 166 of the third injector 153 can then be moved to decrease the volume of the third reservoir 156, thereby forcing the second mixture through the third flow path 117 (including the second membrane 273) and into the reservoir 174 of the fourth injector 171. The flow of the second mixture through the second membrane 273 can effectively bind the released nucleic acids in the second mixture on the second membrane 273. The binding of the nucleic acids on the second membrane 273 can separate the nucleic acids from one or more contaminants contained in the second mixture. Thus, one or more contaminants of the second mixture can be contained in the reservoir 174 of the fourth injector 171.

The first and second valves 109, 110 can then be selectively rotated to provide a fourth flow path 118 (see FIG. 4C) between the fifth reservoir 175 and one of the second and third reservoirs 155, 156 (respectively) through the first valve 109, the second membrane 273, and the second valve 110. The fifth reservoir 175 of the fifth injector 172 can include one or more fourth reagents. In at least one embodiment, the fourth reagent can include a wash buffer solution. For example, the fifth injector 172 can include from a low of about 0.1 mL, about 0.2 mL, about 0.4 mL, about 0.6 mL, about 0.8 mL, or about 1.0 mL to a high of about 2.0 mL, about 3.0 mL, about 4.0 mL, about 5.0 mL, or more of the solution. The piston 126 of the fifth injector 172 can then be moved to decrease the volume of the fifth reservoir 175, thereby forcing the wash buffer through the fourth flow path 118 and into, for example, the third reservoir 156 of the third injector 153. Thus, the wash buffer can flow through the second valve 110, the second membrane 273, and the first valve 109 before entering the third reservoir 156 of the third injector 153.

The wash buffer can serve to gently separate protein, lipids, and cell debris from the nucleic acids (DNA) bound to the second membrane 273. The wash buffer can be a high or low salt wash buffer. The wash buffer can include a buffering agent, containing Guanidine thiocyanate (GuSCN)/Guanidine hydrochloride (Gu-HCl), salt, 20 mM Tris-HCl, EDTA, and/or alcohol. In at least one embodiment, the salt can be from about 10 mM to about 100 mM NaCl or the like, and the buffering agent can be about 20 mM Tris-HCl.

The sample isolation system 100 can further provide an additional wash buffer to further separate the residual cell debris from the nucleic acids (DNA) on the second membrane 273. For example, the sixth injector 173 can include from a low of about 0.1 mL, about 0.2 mL, about 0.4 mL, about 0.6 mL, about 0.8 mL, or about 1.0 mL to a high of about 2.0 mL, about 3.0 mL, about 4.0 mL, about 5.0 mL, or more of the additional wash buffer. The additional wash buffer can contain ethanol.

To provide the additional wash buffer, the second valve 110 can be selectively rotated to provide a fifth flow path 119 (see FIG. 4D) between the sixth reservoir 176 and the fifth reservoir 175 through the second valve 110. The piston 196 of the sixth injector 173 can then be moved to decrease the volume of the sixth reservoir 176, thereby forcing the second wash buffer through the fifth flow path 119 and into the reservoir 175 of the fifth injector 172.

The first and second valves 109, 110 can then be selectively rotated to provide a sixth flow path 120 (see FIG. 4E) between the fifth reservoir 175 and the reservoir 155, 156 of the second or third injectors 152, 153, respectively. For example, the sixth flow path 120 can flow into the reservoir 156 of the third injector 153. The piston 126 of the fifth injector 172 can then be moved to decrease the volume of the fifth reservoir 175, thereby forcing the second wash buffer through the sixth flow path 120 and into the reservoir 156 of the third injector 153.

The second membrane 273 can now contain the nucleic acids (DNA) released from the first membrane 263. The membrane 273 can be either air-dried, or the vacuum 104 can then be coupled to the third injector 153 and in fluid communication with the second membrane 273 via the bore 102, the reservoir 156, and the valve 109. The vacuum 104 can be adapted to remove the reagents disposed within the third reservoir 156 and/or dry the second membrane 273. The second membrane 273 can then be removed and used for subsequent processes, such as a polymerase chain reaction (PCR) process.

Figure 5:
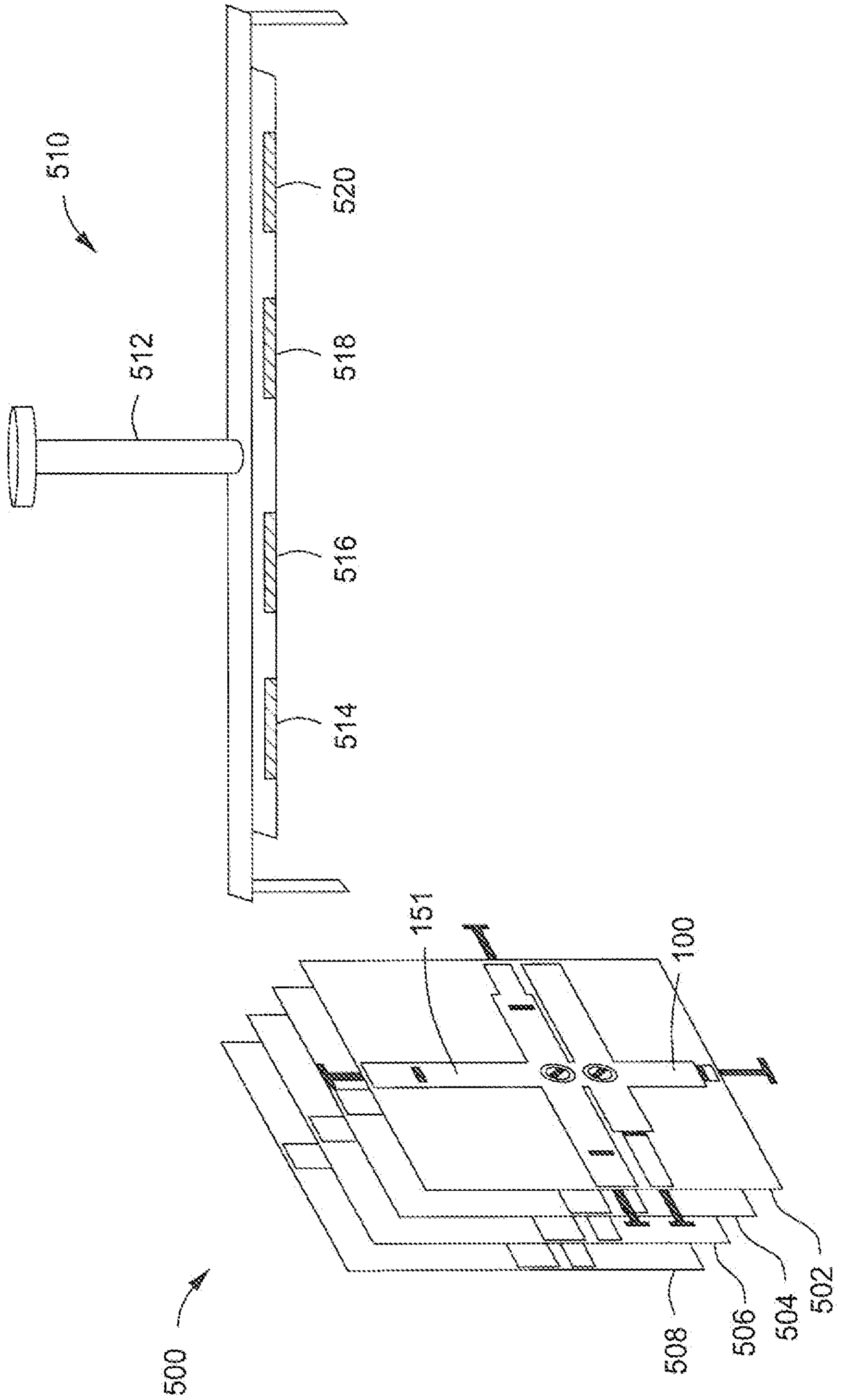
FIG. 5 depicts an illustrative system for operating one or more sample isolation systems at the same or substantially the same time, according to one or more embodiments described.

FIG. 5 depicts an elevational view of an illustrative system 500 for operating one or more sample isolation systems 100 simultaneously, according to one or more embodiments. The system 500 can include a plurality of sample isolation housings (four are shown in FIG. 5 as 502, 504, 506, 508), each adapted to have a sample isolation system 100 disposed therein. One or more actuators (one is shown as 510) can also be coupled to the system 500; however, for purposes of clarity, the actuator 510 is shown separately. Each actuator 510 can include a piston 512 and a plurality of contacts 514, 516, 518, 520. When the piston 512 is pressed, the contacts 514, 516, 518, 520 can move forward and apply a force on, for example, the piston 166 of four first injectors 151 in four different sample isolation systems 100 simultaneously.

Figure 6:
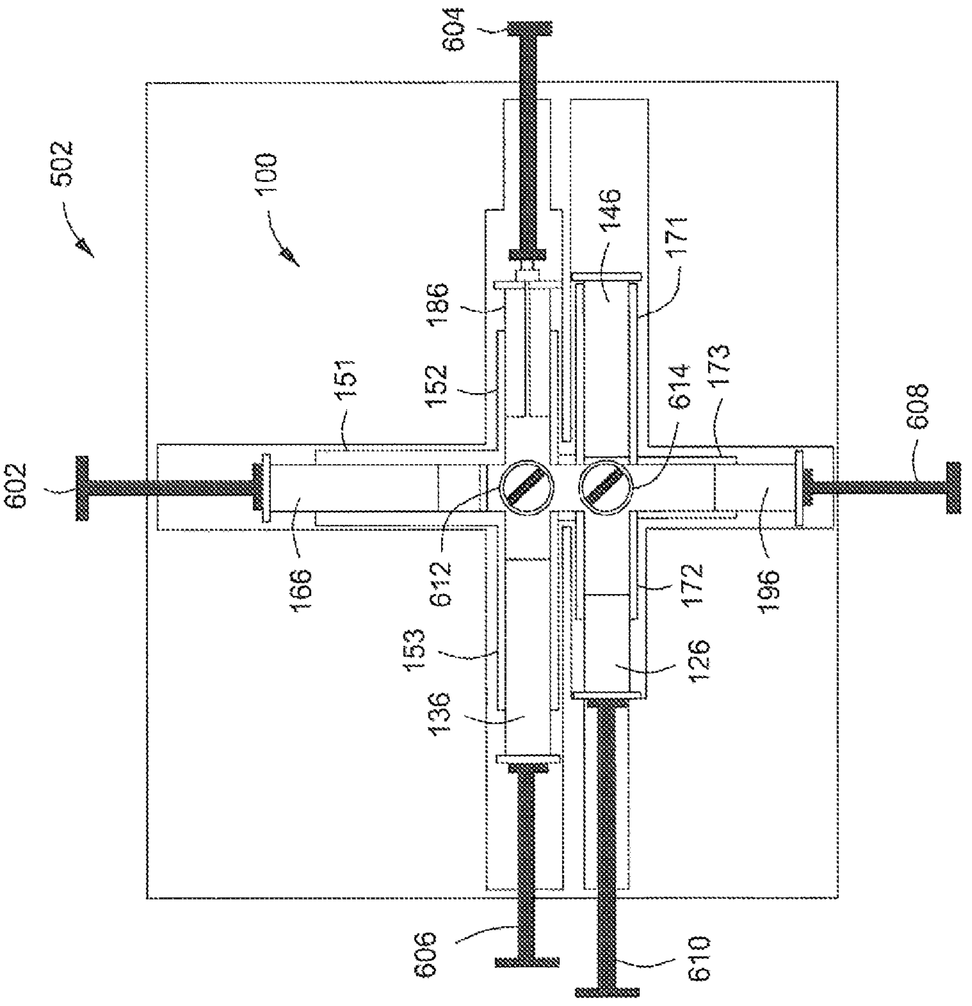
FIG. 6 depicts an elevational view of an illustrative sample isolation housing depicted in FIG. 5, according to one or more embodiments described.

FIG. 6 depicts an elevational view of the illustrative sample isolation housing 502 depicted in FIG. 5, according to one or more embodiments. The sample isolation system 100 can be disposed within the housing 502. The housing 502 can include one or more extension members (five are shown in FIG. 6 as 602, 604, 606, 608, 610) and one or more valve couplings (two are shown as 612, 614). As shown in the embodiment of FIG. 6, each extension member 602, 604, 606, 608, 610 is disposed between a piston 166, 186, 136, 196, 126 (respectively) of an injector 151, 152, 153, 173, 172 (respectively). The extension members 602, 604, 606, 608, 610 operatively connect to the actuator 510 at one of the contacts 514, 516, 518, 520. By way of example, when the actuator 510 moves forward, the contact 514 (if so operatively connected thereon) can move an extension member 602 forward, which in turn, moves the piston 166 of the first injector 151 of the sample isolation system 100. Thus, as the actuator 510 moves forward, the associated multiple contacts (such as 514, 516, 518, 520 of FIG. 5) can move the correspondingly connected extension members (such as one of 602, 604, 606, 608, 610) in multiple sample isolation housings. In a similar way, the valve couplings 612, 614 can be adapted to actuate the valves 109, 110 of multiple sample isolation systems 100 simultaneously.

Figure 7:
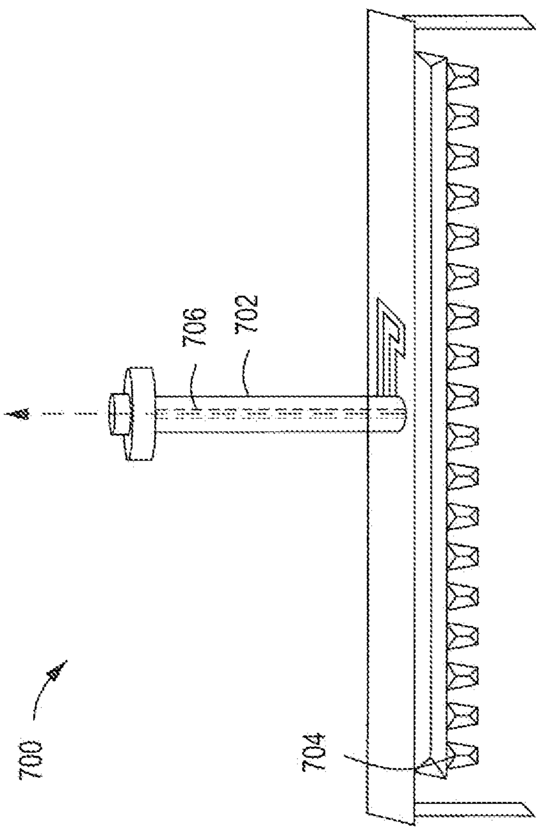
FIG. 7 depicts a cross-sectional view of another illustrative actuator, according to one or more embodiments described.

FIG. 7 depicts a cross-sectional view of another illustrative actuator 700, according to one or more embodiments. The actuator 700 can include a piston 702 and a plurality of contacts 704. For example, the contacts 704 can be male luer locks. When the piston 702 is pressed, the contacts 704 can move forward and apply a force on, for example, multiple extension members (602, 604, 606, 608, 610) and/or multiple pistons (126, 136, 146, 166, 186, 196).

In at least one embodiment, a bore 706 can be formed through the piston 702 providing a flow path therethrough. A vacuum (similar to vacuum 104 of FIG. 1) can be coupled to the piston 702 and adapted to dry the membrane 273 via the flowpath through the bore 706 and the contacts 704.

Figure 8:
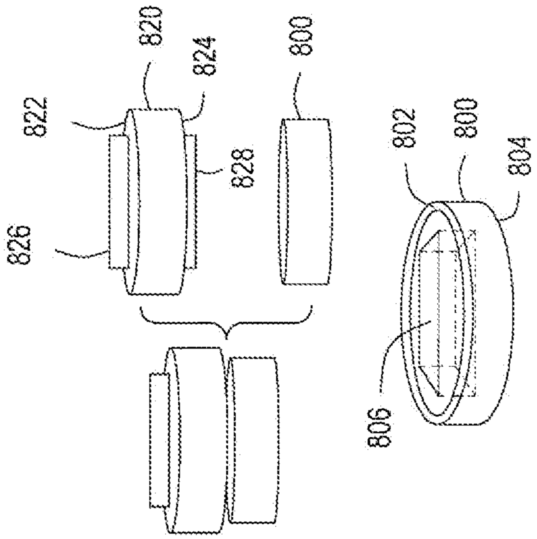
FIG. 8 depicts an illustrative valve coupling disposed proximate a valve of the sample isolation system, according to one or more embodiments described.

FIG. 8 depicts an illustrative valve coupling 800 disposed adjacent a valve 820 of the sample isolation system 100, according to one or more embodiments. The valve 820 can be similar to the valves 109, 110 of FIG. 1. In at least one embodiment, the valve coupling 800 and the valve 820 can interact via a male-female connection. For example, the valve 820 can include a first surface 822 and a second surface 824 having one or more protrusions 826, 828 extending therefrom. The valve coupling 800 can include first and second surfaces 802, 804, each including a recess (only one is shown in FIG. 8 as 806) extending into the valve coupling 800. As such, the protrusion 828 on the valve 820 can fit within the recessed space 806, in the valve coupling 800 so that when the valve coupling 800 is turned, the valve 820 turns as well. As may be appreciated by a skilled artisan having the benefit of the description contained herein, a valve coupling 800 can be disposed between any two valves 800 in the system 500 so that a plurality of valves 800 in multiple, adjacent sample isolation systems 100 can be turned simultaneously.

Various terms have been defined above. To the extent a term used in a claim is not defined above, it should be given the broadest definition persons in the pertinent art have given that term as reflected in at least one printed publication or issued patent. Furthermore, all patents, test procedures, and other documents cited in this application are fully incorporated by reference to the extent such disclosure is not inconsistent with this application and for all jurisdictions in which such incorporation is permitted.

Although only a few exemplary embodiments have been described in detail above, those skilled in the art will readily appreciate that many modifications are possible in the exemplary embodiments without materially departing from the novel teachings and advantages of this invention. Accordingly, all such modifications are intended to be included within the scope of this invention as defined in the following claims. In the claims, means-plus-function and step-plus-function clauses are intended to cover the structures or acts described herein as performing the recited function and not only structural equivalents, but also equivalent structures. Thus, although a nail and a screw may not be structural equivalents in that a nail employs a cylindrical surface to secure wooden parts together, whereas a screw employs a helical surface, in the environment of fastening wooden parts, a nail and a screw may be equivalent structures.

What is claimed is:

1. A sample isolation system, comprising:

an air-tight enclosure;

first and second membranes disposed within the enclosure;

first, second, third and fourth reservoirs disposed within the enclosure, wherein each reservoir is adapted to contain one or more reagents therein;

a first multi-way valve disposed within the enclosure and in fluid communication with the first or second or third reservoirs, and in fluid communication with the first or second membranes or both, wherein the first multi-way valve is configured for providing a first bidirectional flowpath between the first reservoir and the second reservoir and for providing a second bidirectional flowpath between the first reservoir and the third reservoir, wherein the first multi-way valve is adapted to selectively regulate flow of one or more reagents from the first reservoir, through at least one of the first and second membranes, and into the second reservoir; and a second valve disposed within the enclosure and in fluid communication with the third and fourth reservoirs and the first multi-way valve, and in fluid communication with the first or second membranes or both, wherein the second valve is adapted to selectively regulate flow of one or more reagents from the third reservoir, through at least one of the first and second membranes, and into the fourth reservoir.

2. The sample isolation system of claim 1, wherein the first membrane comprises a proteinase membrane.

3. The sample isolation system of claim 1, wherein the second membrane comprises a binding membrane.

4. The sample isolation system of claim 1, wherein the first membrane is disposed between the first reservoir and the first valve.

5. The sample isolation device of claim 1, wherein the second membrane is disposed between the first and second valves.

6. The sample isolation device of claim 1, wherein the first membrane is disposed within a first membrane support assembly, and the second membrane is disposed within a second membrane support assembly, and wherein the first valve is threadably engaged to the first and second membrane support assemblies.

7. The sample isolation system of claim 1, further comprising a reagent disposed within the first reservoir, wherein the reagent is selected from the group comprising a phosphate buffer solution, a salt, a detergent, an alcohol, a protease, a lysis buffer, or a combination thereof.

8. The sample isolation system of claim 1, further comprising a reagent disposed within the second reservoir, wherein the reagent comprises at least one of a lysis buffer and an alcohol solution.

9. The sample isolation device of claim 1, wherein the first and second valves each comprise a rotatable housing having at least one bore disposed therethrough.

10. A method of isolating nucleic acids from a sample, comprising:

placing the sample into the sample isolation system of claim 1;

flowing a first reagent from a first reservoir through a first membrane and a first valve and into a second reservoir containing a second reagent to form a first mixture including the first and second reagents; and flowing the first mixture through the first valve, a second valve, and a second membrane and into a third reservoir.

11. The method of claim 10, further comprising rotating the first valve prior to flowing the first mixture into the third reservoir.

12. The method of claim 10, wherein flowing the first reagent through the first membrane further comprises releasing nucleic acids from the first membrane such that the nucleic acids become disposed within the first mixture.

13. The method of claim 12, wherein flowing the first mixture through the second membrane further comprises binding at least a portion of the nucleic acids disposed within the first mixture to the second membrane.

14. The method of claim 13, further comprising flowing a wash buffer solution through the second membrane.

15. The method of claim 14, further comprising drying the second membrane with a vacuum.

16. A sample isolation system, comprising:

an air-tight enclosure;

first and second membranes disposed within the air-tight enclosure;

a first injector comprising a first reservoir;

a second injector comprising a second reservoir;

a third injector comprising a third reservoir;

a fourth injector comprising a fourth reservoir;

a fifth injector comprising a fifth reservoir;

wherein the first, second, third, fourth, and fifth reservoirs are disposed within the enclosure, and wherein each reservoir is adapted to contain one or more reagents therein;

a first multi-way valve disposed within the enclosure and positioned in fluid communication with the first reservoir and the second reservoir and the third reservoir and the fourth reservoir and in fluid communication with the first membrane and the second membrane, wherein the first multi-way valve is configured for providing a first bidirectional flowpath between the first reservoir and the second reservoir and for providing a second bidirectional flowpath between the first reservoir and the third reservoir, wherein the first multi-way valve is adapted to selectively regulate flow of one or more reagents from the first reservoir, through at least one of the first and second membranes, and into the second reservoir; and a second multi-way valve disposed within the enclosure and positioned in fluid communication with the third reservoir and the fourth reservoir and the fifth reservoir and in fluid communication with the first multi-way valve and the second membrane, wherein the second multi-way valve is configured for providing a third bidirectional flowpath between the third reservoir and the fourth reservoir and for providing a fourth bidirectional flowpath between the fourth reservoir and the fifth reservoir, wherein the second multi-way valve is adapted to selectively regulate flow of one or more reagents from the third reservoir, through at least one of the first multi-way valve and the second membrane, and into the fourth reservoir.

* * * * *